United States Patent [19]

Wright

[11] Patent Number: 4,992,375
[45] Date of Patent: Feb. 12, 1991

[54] METHOD OF REGENERATING SOYBEANS FROM CULTURED SOYBEAN COTYLEDONARY NODES

[75] Inventor: Martha S. Wright, St. Louis, Mo.

[73] Assignee: Monsanto Company, St. Louis, Mo.

[21] Appl. No.: 634,854

[22] Filed: Jul. 26, 1984

Related U.S. Application Data

[63] Continuation-in-part of Ser. No. 555,219, Nov. 25, 1983.

[51] Int. Cl.$^5$ .............................................. C12N 5/00
[52] U.S. Cl. ........................... 435/240.5; 435/240.48; 435/240.49; 435/240.54
[58] Field of Search .................. 435/240, 241, 240.48, 435/240.49, 240.54, 240.5

[56] References Cited

U.S. PATENT DOCUMENTS

| | | | |
|---|---|---|---|
| 3,846,937 | 11/1974 | Staba et al. | 47/58 |
| 4,003,156 | 1/1977 | Sibi et al. | 47/58 |
| 4,038,778 | 8/1977 | Kadkade | 47/58 |
| 4,060,933 | 12/1977 | Kadkade | 47/58 |
| 4,204,366 | 5/1980 | Janick et al. | 47/58 |
| 4,217,730 | 8/1980 | Abo El-Nil | 47/58 |
| 4,241,536 | 12/1980 | Saint-Firmin | 47/58 |
| 4,326,358 | 4/1982 | Lawrence, Jr. et al. | 47/58 |

OTHER PUBLICATIONS

*The Yearbook of Agriculture* 1961 U.S. Dept. Agriculture (Plate).
Poehlman 1959 *Breeding Field Crops* Holt & Co. NY p. 222.
S. L. Kimball & E. T. Bingham, "Adventitious Bud Development of Soybean Hypocotyl Sections in Culture", Crop Science, 13:758–760 (Nov.–Dec. 1973).
"Successful Induction of the Plantlets from the Callus of Soya Hypocotyl", ACTA Botanica Sinica 18:258–262 (1976).
T. H. Oswald, A. E. Smith and D. V. Phillips, "Callus and Plantlet Regeneration from Cell Cultures of Ladino Clover and Soybean", physiol Plant 39:129–134 (1977).
W. D. Beversdorf & E. G. Bingham, "Degrees of Differentiation Obtained in Tissue Cultures of Glycine Species", Crop Science 17: 307–311 (1977).
Hitoshi Saka & Tsai-Ying Cheng, "Regeneration of Soybean–(Glycine Max. L. Merr.) in Culture" –Abstract Only 1980.
Tsai-Ying Cheng, Hitoshi Saka & Thanh H. Vogui--Dinh, "Plant Regeneration from Soybean Cotyledonary Node Segments in Culture", Plant Science Letters 19:91–99 (1980).
Hitoshi Saka, Tranh H. Vogui-Dinh and Tsai-Ying Cheng "Stimulation of Multiple Shoot Formation on Soybean Stem Nodes in Culture", Plant Science Letters, 19:193–201 (1980).
T. Kameya and J. Widholm, "Plant Regeneration from Hypocotyl Sections of Glycine Species", Plant Science Letters, 21:289–294 (1981).
David Evans, "Soybean Genetics Newsletter" Report from Campbell Institute for Research & Techology, vol. 8 1981.
P. Kahlon and S. M. Bhatti, "Effect of Cytokinins on Conditioned Hypocotyls and Cotyledonary Nodes of Soybean", Annual Meetings Abstracts, Jun. 1981.
Phillips, G. C. and Collins, G. B., "Induction and Development of Somatic Embryos from Cell Suspension Culture of Soybean", Plant Cell Tissue Organ Culture 1:123–129 (1981).
K. K. Kartha, K. Pahl, N. L. Leung, and L. A. Mroginski, "Plant Regeneration from Meristems of Grain Legumes: Soybean, Cowpea, Peanut, Chickpea and Bean", Can J Bot 59:1671–1679 (1981).
B. D. Reynolds, W. J. Blackmon and A. M. Lawrence, "Production of Embryoids from Primary & Callus Explants of Soybeans", Abstract Only. Hort. Sciece vol. 17.(3), Jun. 1982.
J. M. Widholm and S. Rick, "Shoot Regeneration from Glycine Canescens Tissue Cultures", Plant Cell Reports pp. 19–20, Springer–Verlag vol. 2, 1983. 1983.
T. M. Curry, S. M. Bhatti and P. S. Kahlon, "Effect of NaCl on Soybean Cells in Suspension Culture and on the Regenerative Ability of Intercotyledonary Nodes", Annual Meeting Abstracts, p. 264. 1984.
Gamborg, O. L., et al. "Somatic Embryogensis in Cell Cultures of Glycine Species", Plant Cell Reports 2:209–212 (1983).
Wilmar, C. anmd M. Hellendoorn, "Growth and Morphogenisis of Asparagus Cells Culture In–Vitro", Nature 217:369–370 (1968).
Christianson, M. L., et al., "A Morphogenetically Competent Soybean Suspension Culture" Science, 222:632–634 (1983).
Street (Editor) 1974 "Tissue Culture and Plant Science" Academic Press pp. 314–327 (Particularly pp. 315–319).
Phillips et al. 1979 "In Vitro Tissue Culture of Selected Legumes and Plant Regeneration from Callus Cultures of Rec Clover", Crop Science, vol. 19, pp. 59–64.
Evans et al. (Editors) 1983 "Handbook of Plant Cell Culture", vol. 1, pp. 205–227 (Particularly p. 212).

*Primary Examiner*—Charles F. Warren
*Assistant Examiner*—David T. Fox
*Attorney, Agent, or Firm*—Dennis R. Hoerner, Jr.; Larry R. Swaney; Howard C. Stanley

[57] ABSTRACT

A method for regenerating soybean plants from cotyledonary nodes is disclosed. Soybean seeds are germinated on nutrient medium containing a cytokinin to produce a donor plant. The cotyledonary nodes of the donor plant are excised and divided into pieces. The cotyledonary node pieces are cultured on nutrient medium containing a cytokinin until callus tissue develops which contains shoots. The shoots are removed and rooted on nutrient medium free of exogenous hormone to form a plantlet.

10 Claims, No Drawings

METHOD OF REGENERATING SOYBEANS FROM CULTURED SOYBEAN COTYLEDONARY NODES

This application is a continuation-in-part of application Ser. No. 555,219 filed Nov. 25, 1983, now abandoned.

BACKGROUND OF THE INVENTION

The present invention relates to the production of soybean plants via tissue culture techniques, and more specifically, to a method of regenerating soybean plants from cultured soybean cotyledonary nodes.

Soybean, *Glycine max*, is an important annual legume whose seeds are valuable for the production of oil and protein. Despite extensive effort, researchers have had limited success in regenerating soybean plants from tissue culture and the methods which have been developed for regeneration of soybeans from tissue culture have little practical utility. This is unfortunate since in vitro tissue and cell culture methods are potentially useful tools in soybean breeding programs, particularly for the multiplication of hybrid germplasm.

In the case of plant regeneration of soybean, only limited success has been reported from either callus or cell suspension culture. Cheng, et al., *PLANT SCIENCE LETTERS*, 19:91-99 (1980) reports a technique for soybean plant regeneration from cotyledonary node segments. The method involves germinating soybean seeds for approximately four weeks on a modified Gamborg media containing sucrose as the carbon source. The basal media was supplemented with 0.025 $\mu$M indole-3-butyric acid (IBA) and benzylaminopurine (BAP) at a concentration of from 0.2 $\mu$M to 20 $\mu$M. The cotyledonary node segments were prepared from the cultured soybean seedlings by removing the cotyledons adjacent to the stem axis, and cutting the stem approximately 3 mm above and below the node region. The cotyledonary node segments excised from the conditioned seedlings were cultured for four weeks on Gamborg medium supplemented with 0.025 $\mu$M IBA and from 0.2 $\mu$M to 20 $\mu$M BAP and then transferred to a medium with 1.0 $\mu$M BAP. At low BAP concentrations (i.e., less than 5.0 $\mu$M), the extent of stimulation of shoot-bud formation differed among the tested soybean cultivars. The authors found that conditioned cotyledonary node segments derived from seedlings cultured with a high BAP concentration were most advantageous for stimulation of shoot-bud formation.

Cheng, et al., concluded that a high concentration of BAP is effective in stimulating bud formation but that it inhibits bud growth. When Cheng, et al., subsequently rooted shoots excised from cotyledonary node cultures of cultivars of Dare and Amsoy soybean cultures, the shoots rooted on basal media without addition of auxin. However, while the plants form the cultivar Dare appeared normal, plants from the cultivar Amsoy were abnormal in that the roots were enlarged in their upper regions and were covered with hairlike white cells and split to the core. Further, Cheng et al., often had difficulty in getting the shoots to root at all.

Phillips and Collins, 1981, reported a system of induction and development of somatic embryos from cell suspension cultures of soybean. The suspension cultures were used as inoculum sources for growing callus on agar-solidified nutrient media. The authors reported that numerous embryoids, particularly of *Glycine soja*, were produced on basal media supplemented with 100 ppm casein hydrolysate, 0.1 $\mu$M abscisic acid, 2.25 $\mu$M 2,4-dichlorophenoxyacetic acid, and 15.0 $\mu$M adenine or 0.46 $\mu$M kinetin. Callus recovered from the suspension culture produced one shoot structure when grown on a solid medium containing 0.2 $\mu$M Amo 1618, an inhibitor of gibberellin synthesis and 80.0 $\mu$M glutathione. The shoot structure consisted of two distinct buds, one producing two leaves. The shoot did not develop into a plant, thus, regeneration of soybean plants was not achieved.

Unlike the prior art methods which yield either no regeneration of soybean plants or regeneration at very low frequencies, often with abnormal soybean plants produced, the method of soybean regeneration described herein offers an efficient, high frequency method which results in the production of normal, healthy soybean plants.

Through the use of the method described herein, one is able to clone multiple individual soybean plants from a single mother plant, e.g., a hybrid (F1). Because the progeny are apparently genetically identical to the mother plant, many transplantable individuals (about 70 to 170), rather than a single individual, may be realized for earlier field evaluation of soybean hybrids. The need for the sexual cycle is totally negated and, thus, no genetic segregation will occur. This, in turn, negates the need for "roguing" of abberant individuals in the field. The procedure thus affords a 30 to 100 fold time savings in manual crossing and deletes one generation of the seed increase process. In the F2 generation, approximately 35,000 individuals can be evaluated, compared to 100 (assuming a single field-grown plant produced a total of 100 seeds). Total time saved in the breeding and hybrid evaluation time cycle could be at least five years.

Another use of the method of this invention is long-term unique germplasm preservation, including all of the ramifications of continuing to produce individuals with identical genotypes over a relatively long period, thus allowing multiple evaluations. Through the use of the procedure described herein, soybean regeneration has been observed from tissue culture for more than ten months. At the present time, nodal tissue has not been maintained in culture past ten months; however, it is expected that the tissue could be maintained in culture for extended periods of time while retaining regeneration capacity.

It will be apparent to skilled artisans that the method of this invention may be used for a variety of purposes. For example, the method described herein may be advantageously employed in a screening program directed to identifying and evaluating chemicals for biological activity in soybeans. Because the method yields shoots, buds, plantlets, and finally plants, chemicals may be screened in vitro at various stages of soybean development. Since the screening is done in vitro rather than in vivo, variability associated with uncontrolled environmental factors may be reduced as well as cost and time necessary for field testing.

Certain of the terms used in this patent specification are defined below; the definitions are believed to be the ones most commonly used by workers skilled in this art.

A "bud" is an undeveloped shoot comprised of a meristem which gives rise to a shoot.

A "cotyledon" is a part of the embryo and is a fleshy specialized leaf-like storage organ which provides nutrients during early seed germination.

A "cotyledonary node" is that part of the seedling including the embryonic axis to which the cotyledons are attached and which botanically defines the division of the hypocotyl and the epicotyl.

"Callus" is a mass of growing cells which may contain organized cells or cells at various stages of cytodifferentiation.

A "cytokinin" is a substance which, in combination with auxin, stimulates cell division in plants and which interacts with auxin in determining the direction which differentiation of the cell takes. All known naturally occurring cytokinins are adenine derivatives (i.e., they are 6-substituted amino-purines).

An "explant" is a piece of tissue taken from a donor plant which in culture will often produce a callus.

An "epicotyl" is the portion of the seedling above the cotyledons which develops into the shoot and its derivatives.

A "hypocotyl" is that portion of the stem of a plant embryo or seedling below the cotyledons and above the root.

A "meristem" is the undifferentiated, mitotically active tissues of a plant.

A "shoot" is derived from meristematic tissue (apical, lateral, or adventitious) and produces the above-ground portion of the plant.

BRIEF SUMMARY OF THE INVENTION

The present invention is directed to a method of regenerating soybean plants from callus culture. Briefly, the method comprises the following steps:

a. germinating soybean seeds on nutrient medium containing a cytokinin as for example kinetin, benzyladenine or derivatives thereof to produce a donor plant;

b. excising the cotyledonary node region from said donor plant;

c. culturing the excised nodal tissue on a nutrient media containing a cytokinin as for example kinetin, benzyladenine or derivatives thereof until callus tissue develops which contains shoots; and d. removing said shoots from said callus and rooting said shoots in a medium free from exogenous hormone to form a plantlet.

DETAILED DESCRIPTION OF THE INVENTION

Soybean seeds were surface sterilized according to the following procedure. Soybean seeds (*Glycyne max* were rinsed with a dilute detergent for 4 to 5 minutes and thereafter the dilute detergent solution was poured off. ("Alconox" is a biodegradable laboratory detergent sold by Alconox, Inc., New York, N.Y., 10003; "Sparkleen" is also a biodegradable laboratory detergent manufactured by Calgon Corporation for Fisher Scientific, Pittsburgh, Pa. 15219.) The seeds were then placed in a 70% solution of isopropyl alcohol and swirled for 1 minute 15 seconds. The alcohol solution was then poured off and a 40% Clorox ® brand bleach solution (5.25% solution of sodium hypochlorite, sold by Clorox company, Oakland, Calif. 94623) containing a nonionic surfactant, three drops of "Tween 20" (polyoxyethylene (20) sorbitan monolaurate nonionic emulsifier manufactured by ICI Americas, Inc., Wilmington, Del. 19897) per 100 ml of Clorox bleach was poured over the seeds and the seeds were swirled for 10 minutes. Thereafter, the Clorox solution was poured off and the seeds were rinsed three to five times with sterile distilled water.

After surface sterilization, the soybean seeds were germinated on agar solidified modified Murashige and Skoog medium (MS or ½MS) containing 5 μM benzyladenine (MS/5BA). The composition of the modified MS medium is shown in Table I. The soybean seeds were placed on a Petri plate (100×25 mm) containing the medium.

TABLE I

| COMPOSITION OF MODIFIED MURASHIGE AND SKOOG MEDIUM | | |
|---|---|---|
| | MS Mg/L | ½MS Mg/L |
| MAJOR ELEMENTS | | |
| $KNO_3$ | 1,900.00 | 950.00 |
| $NH_4NO_3$ | 1,650.00 | 825.00 |
| $MgSO_4.7H_2O$ | 370.00 | 185.00 |
| $CaCl_2.2H_2O$ | 440.00 | 220.00 |
| MINOR ELEMENTS | | |
| $MnSO_4.H_2O$ | 16.90 | 8.45 |
| $H_3BO_3$ | 6.20 | 3.10 |
| $ZnSO_4.7H_2O$ | 8.60 | 4.30 |
| KI | 0.84 | 0.42 |
| $CuSO_4.5H_2O$ | 0.025 | 0.0125 |
| $Na_2MoO_4.2H_2O$ | 0.250 | 0.125 |
| $CoCl_2.6H_2O$ | 0.025 | 0.0125 |
| ORGANIC | | |
| Myo-Inositol | 250.00 | 250.00 |
| Thiamine HCl | 2.50 | 2.50 |
| IRON | | |
| Sequesterene ® | 28.00 | 14.00 |
| PHOSPHATE | | |
| $KH_2PO_4$ | 170.00 | 85.00 |
| SUCROSE | 30,000.00 | 30,000.00 |
| AGAR | 8,000.00 | 8,000.00 |
| pH | 5.50 | 5.50 |

After 14 days, the cotyledonary nodes were excised from the seedlings by removing the epicotyl region within about 2 to about 3 mm of the cotyledonary node and the hypocotyl region within about 1 mm of the node. Portions of the cotyledons were removed by trimming within about 5 mm of the nodal region and any axillary shoots were trimmed flush with the node. The final piece of tissue cultured was a 0.5 to 1.0 cm piece which was dissected into quadrants and placed basally on MS in a 60×15 mm or 100×15 mm Petri plate. The medium contained 5 μM BA and is hereinafter referred to as MS/5BA. After seven days, the quadrants were subcultured on a fresh Petri plate containing $MS_f$/5BA medium; $MS_f$/5BA is the basic MS media in which fructose has been substituted for sucrose as the carbohydrate source. Twenty-one days later shoot and bud counts were taken and the quadrants were transferred to $MS_f$/5BA medium and the twenty-one day cycle was repeated. The shoots were removed to a rooting medium. The light conditions were 12 hours of light, approximately equal to 39 μE/meter$^2$/sec., 12 hours of dark, with the temperature maintained between 21° C. to 25° C. The previously discribed procedure is schematically outlined in FIG. 1.

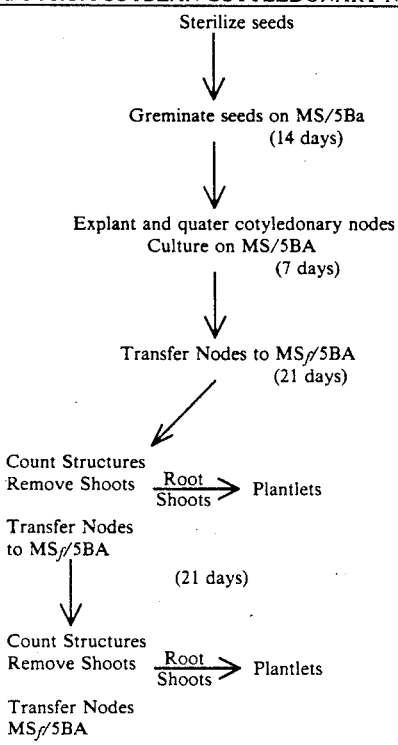

FIGURE 1
PROTOCOL FOR REGENERATION OF SHOOTS AND BUDS FROM SOYBEAN COTYLEDONARY NODES

The shoots were rooted and plantlets were formed as follows. Shoots were rooted in 100×15 mm Petri plates on modified Gamborg medium (MB5) containing no exogenous hormones; the composition of the medium is shown in Table II.

TABLE II

| COMPOSITION OF GAMBORG MEDIUM | |
|---|---|
|  | Mg/L |
| MAJOR ELEMENTS | |
| $KNO_3$ | 250.00 |
| $MgSO_4.7H_2O$ | 250.00 |
| $CaCl_2$ | 150.00 |
| $(NH_4)_2SO_4$ | 134.00 |
| MINOR ELEMENTS | |
| $MnSO_4.H_2O$ | 10.00 |
| $H_3BO_3$ | 3.00 |
| $ZnSO_4.7H_2O$ | 2.00 |
| KI | 0.80 |
| $CaSO_4$ | 0.03 |
| $Na_2MoO_4.2H_2O$ | 0.30 |
| $CoCl_2.6H_2O$ | 0.03 |
| ORGANIC | |
| Myo-Inositol | 100.00 |
| Thiamine HCl | 5.00 |
| Nicotinic Acid | 1.00 |
| Pyridoxine HCl | 1.00 |
| IRON | |
| $Fe_2SO_4.H_2O$ | 30.00 |
| $Na_2EDTA$ | 36.00 |
| PHOSPHATE | |
| $NaH_2PO_4.H_2O$ | 150.00 |
| SUCROSE | 30,000.00 |
| AGAR | 8,000.00 |
| pH | 5.50 |

After about one month, the rooted shoots were transferred to fresh MB5-O in plant culture containers for three to four weeks. At this point, the rooted shoots generally exhibited two to three trifoliate leaves and were approximately 6 cm tall. The plantlets were then planted in gravel contained in plastic boxes (4"×12"×9") fitted with covers. The plants were watered daily with one-half strength modified Hoagland's nutrient solution (the composition of Hoagland's solution is shown in Table III) and high humidity was maintained. As the plants adjusted and grew, the humidity was gradually decreased each day until the plants could be placed in pots and subsequently grown to maturity in a greenhouse under standard conditions.

TABLE III

| HOAGLAND'S NUTRIENT SOLUTION ONE-HALF STRENGTH | |
|---|---|
| Element | Mg/L |
| $KNO_3$ | 303.50 |
| $NH_4H_2PO_4$ | 115.00 |
| $MgSO_4.7H_2O$ | 123.50 |
| KCl | 1.85 |
| $H_3BO_3$ | 0.75 |
| $MnSO_4.H_2O$ | 0.17 |
| $ZnSO_4.7H_2O$ | 0.29 |
| $CuSO_4.5H_2O$ | 0.065 |
| $NaMoO_4.2H_2O$ | 0.055 |
| Sequesterene ® | 14.00 |
| $Ca(NO_3)_2.4H_2O$ | 472.00 |

The practice of the method of this invention results in the production of a high number of shoots which may subsequently be rooted to produce soybean plantlets and finally mature plants.

The formation of shoots in the cotyledon node culture system of this invention is due to de novo bud initiation which begins during germination and continues throughout subsequent culture. De novo formation refers to the fact that the buds are newly formed from a tissue that is not normally involved in bud formation and that the buds were not preformed in the cotyledonary node. The buds arise from the superficial cell layers in a meristematic zone (above and below the existing axillary bud) which was induced during germination. Histologic examination reveals that the meristematic zones develop from 3 to 4 superficial cell layers of the epicotyl and extend out to the cotyledon tissue of the germinated seedlings.

EXAMPLE 1

Following the detailed procedure described above and outlined in FIG. 1, various soybean varieties were examined for their potential to regenerate when treated according to the method of this invention. The medium used for germination was MS/5BA; the excised nodes were divided into quadrants for culturing; the results shown are for four experiments conducted at different times. The ability of all varieties to regenerate is demonstrated, although some varieties regenerate at higher frequencies than others. Table IV summarizes the number of shoots and buds observed at 28 and 49 days culture; data are reported as the mean ± standard error (STE) of 40 quadrants per variety.

TABLE IV

| VARIETY | 28 DAY TOTAL STRUCTURES* | FINAL TOTAL STRUCTURES** |
|---|---|---|
| Wayne | 56.7 ± 6.5 | 84.0 ± 8.2 |
| Mandarin | 26.9 ± 6.0 | 41.9 ± 7.1 |
| Richland | 11.5 ± 8.5 | 9.5 ± 7.9 |
| Roanoke | 51.3 ± 12.6 | 59.3 ± 9.9 |
| Wayne | 40.6 ± 9.1 | 49.6 ± 9.3 |
| CNS | 69.1 ± 7.9 | 94.4 ± 10.3 |
| Manchu | 29.8 ± 10.1 | 21.0 ± 6.3 |

TABLE IV-continued

| VARIETY | 28 DAY TOTAL STRUCTURES* | FINAL TOTAL STRUCTURES** |
|---|---|---|
| Tokyo | 9.1 ± 6.6 | 22.9 ± 8.4 |
| Wayne | 70.7 ± 3.9 | 94.8 ± 5.6 |
| Essex | 48.7 ± 3.4 | 49.2 ± 5.6 |
| Palmetto | 54.4 ± 4.3 | 69.1 ± 4.1 |
| S-100 | 71.4 ± 3.5 | 90.4 ± 6.0 |
| Wayne | 61.4 ± 5.8 | 67.9 ± 6.0 |
| Dunfield | 66.1 ± 5.4 | — |
| Haberlandt | 53.8 ± 6.1 | — |
| Patoka | 47.5 ± 6.5 | 44.3 ± 6.5 |

*Total Structures (TS) = the sum of the 28 day shoot and bud count.
**Final TS = the sum of the 28 day shoot count plus the 49 day shoot and bud count.

The above detailed description of the invention sets forth the preferred conditions for the practice of the process of this invention which will yield the maximum production of shoots which can then be rooted to produce the largest number of regenerated soybean plants. However, as would be recognized by workers skilled in the plant tissue culture art, various changes and/or modifications may be made to the above-described preferred procedure without significantly reducing the quantity or quality of shoots produced and, thus, the quantity of regenerated plants available from practicing the method of the present invention.

As used herein, the term "excise" refers to the preparation of the node tissue which is cultured in the method of the invention; the tissue is prepared as follows: the epicotyl region of a soybean seedling is removed within about 2 to about 3 mm of the cotyledonary node, the hypocotyl region is removed within about 1 to about 2 mm of the node; optionally, portions of the cotyledons may be removed from the node by trimming them within about 5 mm of the nodel region; however, as is illustrated herein, the intact cotyledon may be left on the node with no significant reduction in regeneration capability.

One of the critical features of the present invention is the division of the node tissue into multiple pieces. The number of shoots and, thus, the possible number of regenerated whole plants produced from this system increases significantly when the node is divided into multiple segments. Preferably, the nodes are divided into quadrants; however, further division of the nodes as for example into octants, will yield similar results. Total maceration of the cotyledonary node may be effective if accomplished under gentle conditions; however maceration of the node under certain conditions, e.g., sieving through a screen, appears to decrease the number of shoots observed after 49 days. Example 2 outlines an experiment run to determine the effects of division of the node tissue on shoot production.

EXAMPLE 2

Wayne soybean seeds were germinated on ½MS/5BA for 14 days. Five to 40 nodes per treatment were divided as follows: (1) no division, whole nodes as control; (2) quadrants; (3) four parallel pieces; (4) octants; and (5) sieved through a 60 mesh stainless steel screen. The resulting tissue was cultured on ½MS/5BA for seven days then transferred to fresh ½MS$_f$/5BA agar. Shoot and bud counts were taken, the shoots were then removed, and the tissue transferred to fresh media (½MS$_f$/5BA) for 21 days when counts were again taken. Results obtained from divided nodes show that dissecting the node into quadrants, four parallel pieces, or octants increases regeneration expression 30% to 80% at 28 days and 80% at 49 days. Sieving the nodes through a screen did not negate the regeneration potential but did decrease the expression 75%. The results are shown in Table V; data are reported as mean number of shoots and buds ± standard deviation (STD) observed for each treatment.

TABLE V

EFFECT ON SHOOT AND BUD PRODUCTION OF DIVIDING SOYBEAN COTYLEDONARY NODE EXPLANTS

|  | 28 Days | 49 Days | Number of Replications 28 Days | 49 Day |
|---|---|---|---|---|
| Control, Whole Nodes | 36 ± 7 | 35 ± 7 | 5 | 5 |
| 4 Pieces, Quadrants | 65 ± 2 | 61 ± 2 | 15 | 15 |
| 4 Pieces, Parallel | 48 ± 2 | 61 ± 3 | 15 | 15 |
| 8 Pieces, Octants | 69 ± 6 | 59 ± 25 | 5 | 5 |
| Sieved, 60 Mesh Screen | — | 9 ± 1 | — | 40 |

It is essential that the medium used for germination and especially for culturing the nodes contain certain inorganic macro and micro nutrients. Murashige and Skoog (MS) media shown in Table I is preferred for use herein. However, as would be recognized by those skilled in this art, various other standard plant tissue culture media may be used in the practice of the method described herein. For example, the Gamborg media described in Table II can be used in the practice of the process described herein. For various media see for example Plant Tissue and Cell Culture, 2nd ED., Ed. by H. E. Street, p. 37-44, University of California press (1977). The concentration of inorganic salts in the MS medium can be reduced by about one-half while still retaining good shoot frequency as long as the concentration of benzyladenine is maintained at about 5 μM.

EXAMPLE 3

Full strength MS medium was compared to ½MS medium using whole nodes and nodes divided into quadrants. The procedure followed was as described in Example 1 above. Division of the nodes into quadrants increased the frequency of shoot and bud production over the use of whole nodes in either ½MS/5BA or MS/5BA medium. The frequency of shoots and buds produced using MS medium is significantly greater than that observed using ½MS medium for both whole nodes and quadrants. The results are shown in Table VI; data are reported as the mean ± STD.

TABLE VI

COMPARISON OF NUMBER OF SHOOTS/BUDS PRODUCED USING MS vs. ½MS MEDIA AND WHOLE vs. QUARTERED NODES

| Germ. Media | Final Media | Node | 28 Day Count | 49 Day Count | No. Replicates |
|---|---|---|---|---|---|
| ½MS/5BA | ½MS$_f$/5BA | Whole | 15.4 ± 1.3 | 12.2 ± 0.9 | 22 |
|  |  | Quartered | 62.6 ± 1.3 | 60.6 ± 4.5 | 15 |
| MS/5BA | MS$_f$/5BA | Whole | 28.3 ± 8.0 | 35.3 ± 13.4 | 5* |

TABLE VI-continued

COMPARISON OF NUMBER OF SHOOTS/BUDS
PRODUCED USING MS vs. ½MS MEDIA AND
WHOLE vs. QUARTERED NODES

| Germ. Media | Final Media | Node | 28 Day Count | 49 Day Count | No. Replicates |
|---|---|---|---|---|---|
| | | Quartered | 82.7 ± 12.3 | 91.0 ± 34.8 | 8* |

*Number shown is number of "Experiments"; there were 10 to 20 replications per Experiment.

The frequency of shoot and bud generation is increased by dividing the node into multiple pieces. Additionally, the node should contain at least some of the cotyledon in order to achieve high frequency shoot and bud production.

EXAMPLE 4

Soybean seeds (Wayne) were germinated on MS/5BA medium for 2 weeks. The seedlings were removed and the cotyledonary nodes were prepared for culturing and were cultured as shown in FIG. 2. The results are summarized in Table VII; data are reported as mean ± STE.

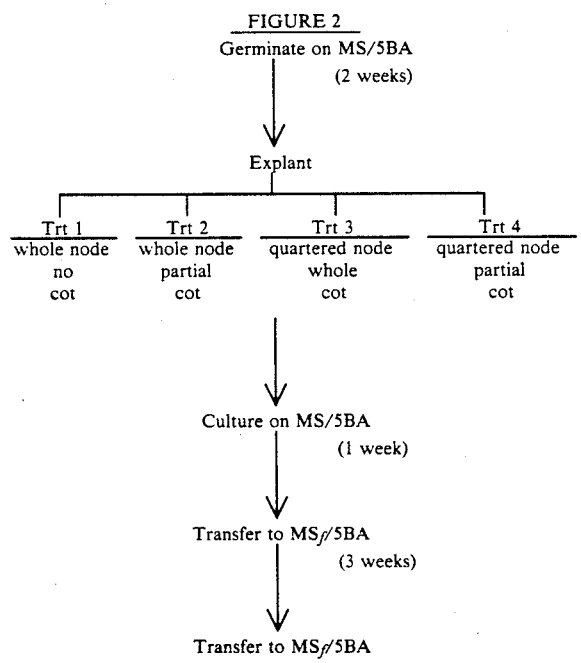

FIGURE 2
Germinate on MS/5BA
(2 weeks)
↓
Explant
Trt 1: whole node, no cot
Trt 2: whole node, partial cot
Trt 3: quartered node, whole cot
Trt 4: quartered node, partial cot
↓
Culture on MS/5BA
(1 week)
↓
Transfer to MSf/5BA
(3 weeks)
↓
Transfer to MSf/5BA

TABLE VII

EFFECT OF COTYLEDON AND QUARTERING
ON TOTAL NUMBER SHOOTS AND
BUDS REGENERATED AFTER 49 DAYS

| Trt No. | No. Nodes | *Total Structures |
|---|---|---|
| 1 | 10 | 28.3 + 2.7 a |
| 2 | 10 | 40.4 + 3.9 a |
| 3 | 10 | 137.3 + 7.1 b |
| 4 | 10 | 142.6 + 9.9 b |

*Total Structures = 28 day shoot count plus the 49 day shoot and bud count; no significant differences exist between treatments with the same letter (Duncan procedure).

Another critical feature of the present invention is the use of a cytokinin in the germination and culturing medium. Germination of the soybean seeds on medium containing for example benzyladenine, benzyladenine riboside, or kinetin is essential to multiple bud production; benzyladenine or a derivative thereof, is preferably used in the practice of the method of the invention. Seeds germinated on medium containing benzyladenine or other cytokinin-like chemicals exhibit a pronounced loss of apical dominance and reduced root growth. Seven days after explant, 75% of the benzyladenine-germinated nodes showed multiple bud production compared to less than 5% of the non-benzyladenine-germinated nodes. In subsequent culture of the excised nodes, only those nodes germinated on benzyl-adenine produced multiple buds.

EXAMPLE 5

This example compares the effect of media, hormones and quartering of the node on the number of shoots and buds produced by the method of the present invention. Soybean seeds (Wayne) were germinated on water or media, with or without hormone for 14 days. Thereafter the seedlings were removed and the node tissue excised as described in Example 1. Whole nodes with no cotyledon tissue (W) were compared with nodes having partial cotyledon tissue which were quartered (Q) as described herein. Table VIII summarizes the treatments and the results observed; the data in Table VII is reported as the mean ± STE.

TABLE VIII

COMPARISON OF BASAL MEDIA EFFECT
OF BA AND QUARTERING NODES

| Trt No. | Germination Media | Explant Media | Explant | Nodes/Trt | Transfer Media | *49 Day Total Structures |
|---|---|---|---|---|---|---|
| 1 | H₂O | MS | W | 30 | MSf | 3.7 ± 0.4 a |
| 2 | H₂O | MS | Q | 21 | MSf | 2.8 ± 0.3 a |
| 3 | H₂O | MS/5BA | W | 30 | MSf/5BA | 3.3 ± 0.5 a |
| 4 | H₂O | MS/5BA | Q | 8 | MSf/5BA | 7.4 1 1.6 ab |
| 5 | H₂O/5BA | MS | W | 7 | MSf | 5.9 ± 1.0 ab |
| 6 | H₂O/5BA | MS | Q | 10 | MSf | 13.5 ± 2.4 abc |
| 7 | H₂O/5BA | MS/5BA | W | 10 | MSf/5BA | 32.8 ± 3.8 d |
| 8 | H₂O/5BA | MS/5BA | Q | 10 | MSf/5BA | 67.7 ± 8.2 f |
| 9 | MS | MS | W | 10 | MSf | 1.9 ± 0.4 a |
| 10 | MS | MS | Q | 8 | MSf | 1.6 ± 0.6 a |
| 11 | MS | MS/5BA | W | 10 | MSf/5BA | 3.2 ± 0.7 a |
| 12 | MS | MS/5BA | Q | 10 | MSf/5BA | 4.9 ± 1.3 a |

TABLE VIII-continued

| | COMPARISON OF BASAL MEDIA EFFECT OF BA AND QUARTERING NODES | | | | | |
|---|---|---|---|---|---|---|
| Trt No. | Germination Media | Explant Media | Explant | Nodes/Trt | Transfer Media | *49 Day Total Structures |
| 13 | MS/5BA | MS | W | 10 | MSf | 3.3 ± 0.7 a |
| 14 | MS/5BA | MS | Q | 10 | MSf | 41.8 ± 6.0 de |
| 15 | MS/5BA | MS/5BA | W | 10 | MSf/5BA | 38.7 ± 2.8 d |
| 16 | MS/5BA | MS/5BA | Q | 10 | MSf/5BA | 89.1 ± 7.4 h |

*Total Structures = 28 day shoot count plus the 49 day shoot and bud count; no significant differences exist between treatments with the same letter (Duncan procedure).

EXAMPLE 6

Following the procedure of Example 1, except that the germination media was ½MS with or without 5BA, the culture media was ½MS/5BA and the final culture media was ½MS/5BA or ¼MS/5BA, the effect of cytokinin in the germination media was studied. The results shown in Table IX are the percentage of nodes displaying shoot and bud production after 14 days germination on ½MS/5BA followed by culture on ½MS/5BA media for seven days; the nodes were thereafter transferred to the final media shown in Table IX. Whole nodes were used in this experiment.

TABLE IX

| EFFECT OF GERMINATION MEDIA ON SHOOT AND BUD PRODUCTION FROM WAYNE COTYLEDONARY NODES | | |
|---|---|---|
| Germination Media (½MS) | Final Media | Percent Nodes With Shoots/Buds |
| + 5 µM BA | ¼MSf/5BA | 75 |
| + 5 µM BA | ½MSf/5BA | 78 |
| + 0 µM BA | ¼MSf/5BA | 0 |
| + 0 LmM BA | ¼MSf/5BA | 5 |

EXAMPLE 7

Following the procedure outlined in Example 2, a derivative of benzyladenine (BAD) having the structure

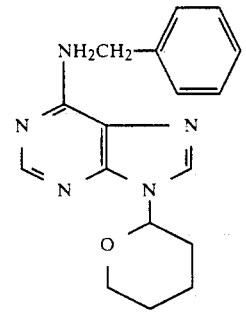

was substituted for benzyladenine in the germination and culture media at a concentration of 5 and 50 µM. Table X summarizes the treatments; the 49 day total structures are reported as the mean ± STE; no significant differences exist between treatments with the same letter (Duncan procedure).

TABLE X

| EFFECT OF A BENZYLADENINE DERIVATIVE ON SHOOT/BUD PRODUCTION | | | | | |
|---|---|---|---|---|---|
| Trt No. | No. Nodes per Trt. | Germination Media | Explant Media | Culture Media | *49 Day Total Structures |
| 1 | 10 | MS/O | MS/O | MSf/O | 1.2 ± 0.6 a |
| 2 | 9 | MS/O | MS/5BA | MSf/5BA | 6.1 ± 2.5 a |
| 3 | 10 | MS/5BA | MS/O | MSf/O | 19.9 ± 2.5 a |
| 4 | 10 | MS/5BA | MS/5BA | MSf/5BA | 147.0 1 7.7 d |
| 5 | 10 | MS/5BA | MS/5BAD | MSf/5BA | 189.5 ± 8.5 e |
| 6 | 10 | MS/5BA | MS/50BAD | MSf/50BAD | 81.4 ± 7.7 b |
| 7 | 10 | MS/5BAD | MS/5BAD | MSf/5BAD | 103.7 ± 8.6 c |
| 8 | 10 | MS/5BAD | MS/5BA | MSf/5BA | 104.7 ± 6.7 c |
| 9 | 10 | MS/50BAD | MS/50BAD | MSf/50BAD | 85.4 ± 10.0 bc |
| 10 | 10 | MS/50BAD | MS/5BA | MSf/5BA | 104.6 ± 7.0 c |

*Total Structures = 28 day shoot count plus 49 day Shoot and bud counts; no significant differences exist between treatments with the same letter (Duncan procedure).

EXAMPLE 8

The effect of various cytokinins was studied to determine which cytokinins or cytokinin-like chemicals produced high frequency shoot and bud production when used in the method of the present invention. The cytokinins zeatin (Z), dihydrozeatin (DHZ), zeatin riboside (ZR), and isopentenyladenine (2iP) at 1, 5, and 10 µM concentration, benzyladenine riboside (BAR) at 5 and 10 µM or kinetin (K) at 5 and 50 µM was substituted for benzyladenine throughout the germination and culturing of the cotyledonary nodes as described in Example 1 through the first shoot and bud counts at 21 days. The results indicate that none of the following cytokinins (Z, DHZ, ZR, or 2iP) at 0.5 to 10 µM substituted for 5 or 10 µM BA in the germination or culturing step. The resulting nodes failed to display broken apical dominance and failed to subsequently produce multiple shoots and buds during culturing. Zeatin (5 µM), zeatin riboside, and isopentyladenine (10 μM) caused death of the nodes. Benzyladenine riboside (BAR) can be directly substituted for benzyladenine (BA) at 5 or 10 μM and although kinetin (K) can be substituted, the level must be higher, on the order of 50 μM, and the response in total structures (shoots and buds) will generally be less. The data shown in Table XI are expressed as the mean number of shoots and buds observed per node ± STD; data are based on ten replications per treatment. The germination medium used was ½MS, and whole nodes were cultured.

TABLE XI
EFFECT OF VARIOUS CYTOKININS SUBSTITUTED FOR BENZYLADENINE IN THE GERMINATION AND CULTURING MEDIUM

| CYTOKININ | [μM] | No. of Buds | No. of Shoots |
|---|---|---|---|
| DHZ | 1 | 0 ± 0 | 0 ± 0 |
|  | 5 | 0 ± 0 | 1 ± 1 |
| Z | .5 | 0 ± 0 | 1 ± 1 |
|  | 1 | 0 ± 0 | <1 ± 1 |
|  | 5 | necrotic | necrotic |
| 2iP | 1 | 0 ± 0 | 1 ± 1 |
|  | 5 | 0 ± 0 | 1 ± 1 |
|  | 10 | necrotic | necrotic |
| K | 5 | 0 ± 0 | 1 ± 1 |
|  | 50 | 5 ± 3 | 6 ± 4 |
| BAR | 5 | 15 ± 3 | 7 ± 5 |
|  | 10 | 25 ± 12 | 2 ± 1 |
| BA | 1 | 5 ± 4 | 6 ± 3 |
|  | 5 | 14 ± 6 | 8 ± 4 |
|  | 10 | 11 ± 3 | 4 ± 3 |

The time period for the germination step will vary from about 7 to about 30 days. The preferred germination period for use herein is 14 days; however, germination periods of from about 7 to about 28 days may be used without adversely affecting the number of shoots and buds produced. Choice of a particular germination period is left to the discretion of a skilled worker. Example 9 describes the effect of germination time on shoot and bud production.

EXAMPLE 9

Following the procedure of Example 1, the seeds were sterilized, germinated on MS/5BA, and explanted. Quartered nodes were cultured. The nodes were explanted at 14 and 28 days after germination onto MS/5BA media for 7 days followed by transfer to MS$_f$/5BA for three weeks and thereafter; shoots and buds were counted (28 day count). Ten nodes were cultured for each treatment. The nodes were transferred to fresh MS$_f$/5BA media and cultured for an additional three weeks and shoots and buds were again counted (49 day count). The results are summarized in Table XII; "total structures" is the mean ± STE of the 49 day shoot and bud count.

TABLE XII
EFFECT OF GERMINATION PERIOD ON NUMBER OF SHOOTS AND BUDS

| Germination Period | Total Structures |
|---|---|
| 14 Days | 114.9 ± 9.0 |
| 28 Days | 110.7 ± 8.8 |

As outlined in Example 10, seeds collected from mature plants produced by the method of the present invention were grown to maturity and the plants were compared to field-grown nonregenerated plants. No differences were observed between progeny of field-grown soybeans as to such quantitative characteristics as germination, flower color, plant height, etc.

EXAMPLE 10

Seven seeds from each of four regenerated parent plants and 25 seeds from field-grown nonregenerated Wayne soybeans were dusted with "Captan" fungicide, cis-N-((trichloromethyl)thio)-4-cyclo-hexene-1,2-dicarboximide fungicide, and planted one seed per 6 inch pot in the greenhouse. After 34 days, the plants were placed under a 14 hour photoperiod to induce flowering and flower color was observed. All the plants were sprayed periodically for thrips with benzene hexachloride (BHC) insecticide and fertilized weekly. After a total of 12 weeks, all plants were observed for height, total pods, total seeds, and total gram weight of seeds. The results are shown in Table XIII below.

TABLE XIII
COMPARISON OF REGENERATED WAYNE SOYBEAN PROGENY (R1) WITH PROGENY OF FIELD-GROWN WAYNE SOYBEAN (FG)

| Quantitative Character | R1* | FG* |
|---|---|---|
| Germination | 89% | 96% |
| Flower Color | White | White |
| 12 Week Plant Height (in.) | 22.7 ± 1.1 | 23.0 ± 1.1 |
| Total Pods/Plant | 23.7 ± 1.5 | 23.5 ± 1.6 |
| Total Seeds/Plant | 48.5 ± 3.8 | 49.8 ± 3.6 |
| Seeds/Pod | 2.0 ± 0.1 | 2.1 ± 0.1 |
| Total Seed Weight, Grams | 9.3 ± 0.8 | 9.8 ± 0.7 |
| Weight/Seed, Grams | 0.2 ± 0.0 | 0.2 ± 0.0 |

*Data are reported as mean ± STE of 19 R1 progeny vs. mean ± STE of 22 FG progeny.

The method of the present invention is applicable across a large variety of commercially available soybean lines. All of the following varieties, one each from 10 maturity groups, Fiskeby 00, Evans 0, Steele I, Amsoy 71 II, Wayne III, Clarke 63 IV, Dare V, Hood VI, Bragg VII, and Hutton VIII, produced multiple shoots and buds when used in the method of the invention. At 49 days, the second count showed that a mean of 21±5 shoots could be produced from any variety tested. Other varieties which have also been tested include Pride, Williams and Geeling 3. All varieties display multiple shoot and bud production. Example 11 outlines the results obtained when 10 varieties were used in the method of the invention.

EXAMPLE 11

Ten whole nodes per variety were explanted and cultured according to the procedure of Example 1 except that ½MS/5BA was used as the germination medium and ½MS$_f$/5BA was used as the culture medium. Shoot and bud counts were taken after 28 days in culture. The results summarized in Table XIV are expressed as the mean total structures of 10 replications ± STD.

TABLE XIV
MATURITY GROUP SURVEY

| Variety | Maturity Group | Total Structures |
|---|---|---|
| Fiskeby | 00 | 19 ± 13 |
| Evans | 0 | 19 ± 3 |
| Amsoy 71 | II | 22 ± 7 |
| Wayne | III | 27 ± 8 |
| Clark 63 | IV | 12 ± 8 |
| Dare | V | 25 ± 6 |
| Hood | VI | 20 ± 11 |
| Bragg | VII | 23 ± 7 |

TABLE XIV-continued

MATURITY GROUP SURVEY

| Variety | Maturity Group | Total Structures |
|---|---|---|
| Hutton | VIII | 14 ± 3 |

Cheng et al reported the regeneration of soybean plants from soybean cotyledonary nodes in culture. Cheng T-Y, Saka H. and Voqui-Dinh T. H., "Plant Regeneration From Soybean Cotyledonary Node Segments In Culture", *Plant Sci Lett* (1980) 19:91-99. See also, Saka H, Voqui-Ding TH, Cheng T-Y, "Stimulation of Multiple Shoot Formation on Soybean Stem Nodes in Culture". *Plant Sci Lett* (1980) 19:193-201 and Saka H., Cheng T-Y, "Regeneration of Soybean (*Glycine max* L Merr.) In Culture", *Plant Physiol (Suppl)* (1980) 65:92, abstract 500. As demonstrated by the following examples, the method of this invention is unexpectedly superior to the method disclosed by Cheng et al. in the total number of shoots and buds produced and thus the number of regenerated soybean plants which may be produced by the method. The procedure used by Cheng et al. for regeneration of soybean plants from cotyledonary nodes is outlined in FIG. 3; this procedure uses the whole node with the cotyledons entirely removed.

FIGURE 3

Following the method of Cheng et al described in FIG. 3, the effect of explanting the node according to the procedure of the present invention and the use of MS/5BA medium in the Cheng et al. method was determined.

EXAMPLE 12

Utilizing the time periods outlined in FIG. 3, soybean seeds were germinated for 28 days on modified Gamborg B5 medium (MB5) containing 0.025 μM of indolebutyric acid plus 20 μM of benzyladenine (MB5/0.025IBA +20 BA) or MB5 containing 5 μM of benzyladenine (MB5/5BA). Nodes were explanted according to Cheng et al., i.e., the whole node with the cotyledons entirely removed (TY). Nodes were also explanted according to the procedure of the invention, in some treatments whole nodes (W) were used, in other treatments quartered nodes (Q) were used. The explants were cultured on MB5 medium containing 0.025 μM of IBA plus 1.0 μM of BA (MB5/0.025 IBA +1 BA) or MB5 containing 5 μM BA (MB5/5BA) for 28 days and shoots and buds were counted; the nodes were then transferred to fresh MB5/0.025 IBA+1BA or MB5/5 BA media and cultured for 21 days whereupon shoots and buds were again counted. The results are summarized in Table XV; "Total Structures" is the mean ± STE of the 28-day shoot count plus the 49-day shoot and bud count.

TABLE XV

TOTAL NUMBER OF SHOOTS AND BUDS PRODUCED USING CHENG PROTOCOL AND EXPLANTING ACCORDING TO INVENTION

| Trt No. | Germination Media | Nodes/ Trt. | Explant Media | Method of Explant | Transfer Media | Total Structures |
|---|---|---|---|---|---|---|
| 1 | MB5/.025IBA + 20BA | 10 | MB5/.025IBA + 1BA | TY | MB5/.025IBA + 1BA | 21.8 ± 2.5 |
| 2 | MB5/.025IBA + 20BA | 10 | MB5/.025IBA + 1BA | W | MB5/.025IBA + 1BA | 21.4 ± 3.5 |
| 3 | MB5/.025IBA + 20BA | 10 | MB5/.025IBA + 1BA | Q | MB5/.025IBA + 1BA | 97.5 ± 3.4 |
| 4 | MS/5BA | 10 | MS/5BA | TY | MS/5BA | 38.4 ± 4.1 |
| 5 | MS/5BA | 10 | MS/5BA | W | MS/5BA | 37.5 ± 4.7 |
| 6 | MS/5BA | 10 | MS/5BA | Q | MS/5BA | 110.7 ± 8.8 |

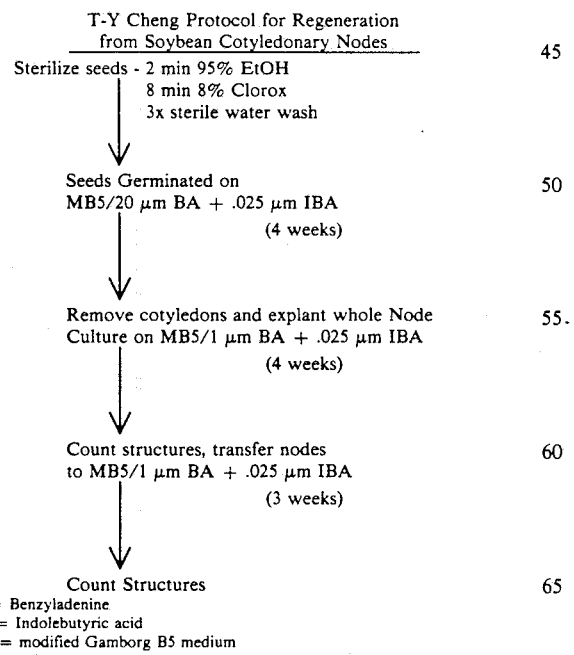

T-Y Cheng Protocol for Regeneration from Soybean Cotyledonary Nodes

Sterilize seeds - 2 min 95% EtOH
  8 min 8% Clorox
  3x sterile water wash
↓
Seeds Germinated on
MB5/20 μm BA + .025 μm IBA
  (4 weeks)
↓
Remove cotyledons and explant whole Node
Culture on MB5/1 μm BA + .025 μm IBA
  (4 weeks)
↓
Count structures, transfer nodes
to MB5/1 μm BA + .025 μm IBA
  (3 weeks)
↓
Count Structures BA = Benzyladenine
IBA = Indolebutyric acid
MB5 = modified Gamborg B5 medium

EXAMPLE 13

Example 12 was repeated utilizing the time periods of the present invention outlined in FIG. 1. The treatments are shown in Table XVI; "Total Structures" are the sum of the 28 shoot counts and 49 day shoot and bud counts, the results are the mean ± STE.

TABLE XVI

TOTAL NUMBER OF SHOOTS AND BUDS PRODUCED
USING METHOD OF THE INVENTION AND EXPLANTING AS SHOWN

| Trt No. | Germination Media | Nodes/Trt | Explant Media | Method of Explant | Transfer Media | Total Structures |
|---|---|---|---|---|---|---|
| 1 | MB5/.025IBA + 20BA | 10 | MB5/.025IBA + 1BA | TY | MB5/.025 IBA + IBA | 44.9 ± 3.4 |
| 2 | MB5/.025IBA + 20BA | 10 | MB5/.025IBA + 1BA | W | MB5/.025 IBA + IBA | 35.5 ± 3.5 |
| 3 | MB5/.025IBA + 20BA | 10 | MB5/.025IBA + 1BA | Q | MB5/.025 IBA + IBA | 112.6 ± 4.9 |
| 3 | MS/5BA | 10 | MS/5BA | TY | MS/5BA | 26.1 ± 2.5 |
| 5 | MS/5BA | 10 | MS/5BA | W | MS/5BA | 46.9 ± 4.7 |
| 6 | MS/5BA | 10 | MS/5BA | Q | MS/5BA | 114.9 ± 9.0 |

The data shown in Tables XV and XVI illustrates that explanting the cotyledonary nodes according to the method of the invention results in unexpectedly superior increase in the number of shoots and buds produced when the method of Cheng et al. is followed.

While the invention has been described in connection with specific embodiments thereof, it will be understood that it is capable of further modification, and this application is intended to cover any variations, uses, or adaptions of the invention following, in general, the principles of the invention and including such departures from the present disclosure as come within known or customary practice in the art to which the invention pertains.

What is claimed is:

1. A method of regenerating soybean plants from callus culture which comprises:
    (a) germinating soybean seeds on nutrient medium comprising a cytokinin to produce a donor plant;
    (b) excising the cotyledonary node from said donor plant by removing the epicotyl region within about 2 mm to about 3 mm of the cotyledonary node, removing the hypocotyl region within about 2 mm of said cotyledonary node, removing the cotyledons within about 5 mm of the node region and then dividing the excised node into pieces;
    (c) culturing a divided node piece on a nutrient medium comprising a cytokinin selected from the group consisting of kinetin, benzyladenine, benzyladenine riboside and a derivative of benzyladenine having the structure

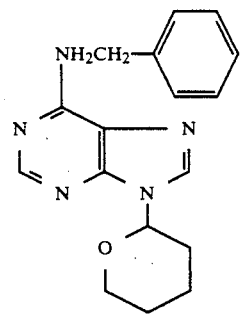

until callus tissue develops which contains shoots; and
    (d) removing said shoots from said callus and rooting said shoots on a nutrient medium free of exogenous hormone to form a plantlet.

2. A method according to claim 1 wherein said nutrient medium is Murashige and Skoog medium.

3. A method according to claim 1 wherein said germination medium comprises a cytokinin selected from the group consisting of benzyladenine, benzyladenine riboside and kinetin.

4. A method according to claim 1 wherein said germination medium comprises from about 5 to about 50 µM of a cytokinin selected from the group consisting of benzyladenine and

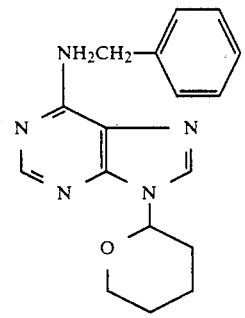

5. A method according to claim 1 wherein said germination medium and said culture medium comprise 5 µM of benzyladenine.

6. A method according to claim 1 wherein said rooting medium is Gamborg medium.

7. A method according to claim 1 wherein said node is divided into about 4 to 8 pieces prior to culturing.

8. A method according to claim 1 wherein said seeds are germinated for from about 7 to about 21 days.

9. A method according to claim 1 wherein said seeds are germinated for about 14 days.

10. A method for regenerating soybean plants from callus culture which comprises:
    (a) germinating soybean seeds for from about 7 to about 21 days on Murashige and Skoog nutrient medium comprising about 5 µM of benzyladenine to produce a donor plant;
    (b) excising the cotyledonary node from said donor plant by removing the epicotyl region within about 2 mm to about 3 mm of the cotyledonary node, removing the hypocotyl region within about 2 mm of said cotyledonary node, removing the cotyledons within about 5 mm of the node region and then dividing said excised node into pieces;
    (c) culturing said pieces on Murashige and Skoog nutrient media comprising about 5 µM of benzyladenine until callus tissue develops which contains shoots; and
    (d) removing said shoots from said callus and rooting said shoots on Gamborg medium free from exogenous hormone to form a plantlet.

* * * * *